(12) United States Patent
Feng et al.

(10) Patent No.: US 11,390,602 B2
(45) Date of Patent: Jul. 19, 2022

(54) N-ALKYL-N-CYANOALKYLBENZAMIDE COMPOUND AND USE THEREOF

(71) Applicant: JIANGSU FLAG CHEMICAL INDUSTRY CO., LTD., Nanjing (CN)

(72) Inventors: Meili Feng, Nanjing (CN); Hongju Li, Nanjing (CN); Xinxin Shi, Nanjing (CN); Linbo Wang, Nanjing (CN); Kaicheng Yao, Nanjing (CN)

(73) Assignee: JIANGSU FLAG CHEMICAL INDUSTRY CO., LTD., Nanjing (CN)

( * ) Notice: Subject to any disclaimer, the term of this patent is extended or adjusted under 35 U.S.C. 154(b) by 32 days.

(21) Appl. No.: 16/958,711

(22) PCT Filed: Dec. 21, 2018

(86) PCT No.: PCT/CN2018/122721
§ 371 (c)(1),
(2) Date: Jun. 28, 2020

(87) PCT Pub. No.: WO2019/128871
PCT Pub. Date: Jul. 4, 2019

(65) Prior Publication Data
US 2021/0009554 A1   Jan. 14, 2021

(30) Foreign Application Priority Data

Dec. 29, 2017 (CN) .......................... 201711498982.1
Dec. 7, 2018 (CN) .......................... 201811502023.7

(51) Int. Cl.
*C07D 401/04* (2006.01)
*A01N 43/56* (2006.01)
*C07C 233/92* (2006.01)

(52) U.S. Cl.
CPC ........... *C07D 401/04* (2013.01); *A01N 43/56* (2013.01); *C07C 233/92* (2013.01)

(58) Field of Classification Search
CPC .............................. C07D 401/04; A01N 43/56
See application file for complete search history.

(56) References Cited

FOREIGN PATENT DOCUMENTS

| CN | 101298451 A | 11/2008 |
|---|---|---|
| CN | 102285965 A | 12/2011 |
| WO | 02070483 A1 | 9/2002 |
| WO | 2008134969 A1 | 11/2008 |
| WO | 2010042699 A1 | 4/2010 |

OTHER PUBLICATIONS

Barret, Roland. Importance and Evaluation of the pKA, 2018, Therapeutical Chemistry, Section 2.4.1.1, p. 28.*
Li et al. Benzamide Compounds and Uses thereof, English Translation of CN 101298451, 2008, pp. 1-16).*
Harold W. Heine, et al., Aziridines. XVI. Isomerization of Some I-Aroylaziridines, Oct. 1967, pp. 3069-3074, vol. 32.
B. Helferich et al. ,Working with Hazardous Chemicals, Organic Syntheses, Coll., 1929, p. 32, vol. 9.
Oliver Thorn-Seshold, et al., A robust, high-sensitivity stealth probe for peptidases, Chemical Communications, 2012, pp. 6253-6255, vol. 48, No. 50.
Qiuzheng Tang, et al., Re/Mg Bimetallic Tandem Catalysis for [4+2] Annulation of Benzamides and Alkynes via C—H/N—H Functionalization, Journal of the American Chemical Society, 2013, pp. 4628-4631, 135(12).
Yuexiu Jiang, et al., Preparation of Ni/bentonite catalyst and its applications in the catalytic hydrogenation of nitrobenzene to aniline, Chinese Journal of Chemical Engineering 24, 2016, pp. 1195-1200, 24(9).
Wei Ronghao, et al., Synthesis of Organic Pigment Intermediate N, N'-bisacetylaceto-2,5-dimenthyl-1,4-phenylenediamine, Dye Industry, 2000, pp. 16-18, 37(4).
Lawrencje J. Exner, et al., a-(N-Alkylamino)-nitriles, J. Am. Chem. Soc., Oct. 5, 1953, pp. 4841-4842, vol. 75.

* cited by examiner

*Primary Examiner* — Samira J Jean-Louis
(74) *Attorney, Agent, or Firm* — Bayramoglu Law Offices LLC

(57) ABSTRACT

The present invention discloses an N-alkyl-N-cyanoalkyl-benzamide compound of General Formula I, an intermediate of General Formula II used to prepare the compound, wherein $R_1$ is selected from halo or $C_1$-$C_3$ alkyl; $R_2$ is selected from halo or CN; $R_3$ is selected from halo, or $C_1$-$C_3$haloalkyl; $R_4$ is selected from halo; $R_5$ is selected from H or halo; $R_6$ is selected from $C_1$-$C_3$alkyl, $C_1$-$C_3$ haloalkyl or $C_1$-$C_5$ alkoxyalkyl; $R_7$ is selected from $C_1$-$C_5$ alkyl; and $R_8$ is selected from hydrogen or $C_1$-$C_5$alkyl. Compared with the compounds in the prior art, the compound of General Formula I has a higher activity at a low concentration. Particularly, the compound of the present invention still has 60% or higher of the insecticidal activity at a concentration below 1 ppm. This greatly reduces the amount of the compound used and the residue of the compound in farmland, and is thus environmentally friendly.

10 Claims, No Drawings

N-ALKYL-N-CYANOALKYLBENZAMIDE COMPOUND AND USE THEREOF

CROSS REFERENCE TO THE RELATED APPLICATION

This application is the national phase entry of International Application No. PCT/CN2018/122721, filed Dec. 21, 2018, which is based upon and claims priority to Chinese Patent Application No. 201811502023.7, filed on Dec. 7, 2018, and Chinese Patent Application No. 201711498982.1, filed on Dec. 29, 2017, the entire contents of which are incorporated herein by reference.

TECHNICAL FIELD

The present invention relates to the technical field of insecticides, and particularly to an N-alkyl-N-cyanoalkylbenzamide compound and use thereof.

BACKGROUND

Resistance of pests has been a problem that puzzles plant protection workers. To solve this problem, new types of insecticides need to be constantly developed. The benzamide compounds developed by DuPont are a new class of compounds that target ryanodine receptor. The representative compound chlorantraniliprole (Rynaxypyr™) shows excellent comprehensive insecticidal activity and field effects, low toxicity to mammals, and good environmental compatibility.

The patent WO 2008134969 discloses N-cyanoalkyl o-aminobenzamide compounds, of which Compound 1.14 (KC1) has good insecticidal activity.

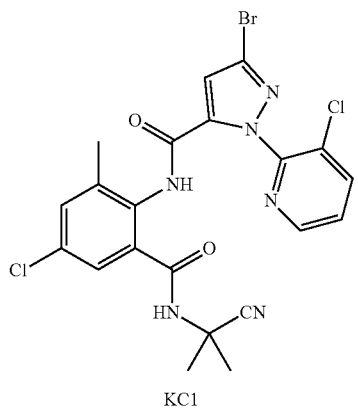

KC1

In the prior art, the N-alkyl-N-cyanoalkylbenzamide compound shown in the present invention has not been disclosed.

SUMMARY

The present invention provides an N-alkyl-N-cyanoalkylbenzamide compound with novel structure and higher insecticidal effect, which is useful in the control of pests.

The following technical solutions are adopted in the present invention. An N-alkyl-N-cyanoalkylbenzamide compound of General Formula I is provided:

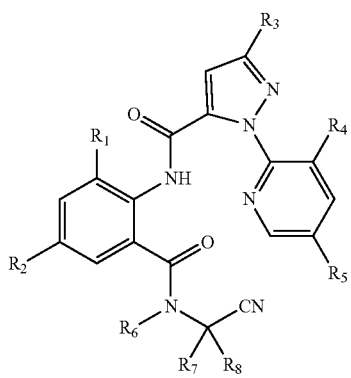

I

In General Formula I:

$R_1$ is selected from halo or $C_1$-$C_3$ alkyl; $R_2$ is selected from halo or CN; $R_3$ is selected from halo or $C_1$-$C_3$ haloalkyl; $R_4$ is selected from halo; $R_5$ is selected from H or halo; $R_6$ is selected from $C_1$-$C_3$ alkyl, $C_1$-$C_3$ haloalkyl, or $C_1$-$C_5$ alkoxyalkyl; $R_7$ is selected from $C_1$-$C_5$ alkyl; and $R_8$ is selected from hydrogen or $C_1$-$C_5$ alkyl. The physical properties of some compounds of General Formula I are shown in Table 1. Some compounds of General Formula I are tested by $^1$H NMR spectroscopy. The results of $^1$H NMR spectroscopy (DMSO-$d_6$, 300 MHz) are shown in Table 3.

The preferred compounds in present invention are those of General Formula I in which $R_1$ is selected from chloro, bromo or methyl; $R_2$ is selected from chloro, bromo, fluoro or CN; $R_3$ is selected from chloro, bromo or trifluoromethyl; $R_4$ is selected from chloro; $R_5$ is selected from H or chloro; $R_6$ is selected from $C_1$-$C_3$alkyl, $CH_2OCH_3$, $CH_2O$ $CH_2CH_3$, $CH_2CH_2OCH_3$, $CF_3$, $CH_2CH_2F$, $CH_2CHF_2$, $CH_2CF_3$, $CF_2CF_3$ or $CF(CF_3)_2$; $R_7$ is selected from methyl; and $R_8$ is selected from hydrogen or methyl.

More preferred compounds are those of General Formula I in which $R_1$ is selected from chloro, bromo or methyl; $R_2$ is selected from chloro, bromo, fluoro or CN; $R_3$ is selected from chloro or bromo; $R_4$ is selected from chloro; $R_5$ is selected from H; $R_6$ is selected from methyl; $R_7$ is selected from methyl; and $R_8$ is selected from methyl.

TABLE 1

The physical properties of some compounds of General Formula I according to the present invention.

| Compound No. | $R_1$ | $R_2$ | $R_3$ | $R_4$ | $R_5$ | $R_6$ | $R_7$ | $R_8$ | Appearance (Melting point (° C.)) |
|---|---|---|---|---|---|---|---|---|---|
| 1.1 | $CH_3$ | Cl | Br | Cl | H | $CH_3$ | $CH_3$ | $CH_3$ | White solid (244.9-245.4) |
| 1.2 | $CH_3$ | Cl | Cl | Cl | H | $CH_3$ | $CH_3$ | $CH_3$ | |

TABLE 1-continued

The physical properties of some compounds of General Formula I according to the present invention.

| Compound No. | $R_1$ | $R_2$ | $R_3$ | $R_4$ | $R_5$ | $R_6$ | $R_7$ | $R_8$ | Appearance (Melting point (° C.)) |
|---|---|---|---|---|---|---|---|---|---|
| 1.3 | $CH_3$ | Cl | $CF_3$ | Cl | Cl | $CH_3$ | $CH_3$ | H | |
| 1.4 | $CH_3$ | Cl | Br | Cl | H | $CH_2OCH_3$ | $CH_3$ | $CH_3$ | |
| 1.5 | $CH_3$ | CN | Br | Cl | H | $CH_3$ | $CH_3$ | $CH_3$ | White solid (256.3-257.0) |
| 1.6 | $CH_3$ | CN | Cl | Cl | H | $CH_3$ | $CH_3$ | $CH_3$ | White solid (263.2-264.9) |
| 1.7 | $CH_3$ | CN | Br | Cl | H | $CF_3$ | $CH_3$ | $CH_3$ | |
| 1.8 | $CH_3$ | CN | Br | Br | Cl | $CF_3$ | $CH_3$ | H | |
| 1.9 | $CH_3$ | Br | Br | Cl | H | $CH_3$ | $CH_3$ | $CH_3$ | White solid (149.8-152.9) |
| 1.10 | $CH_3$ | Br | Cl | Cl | Cl | $CH_3$ | $CH_3$ | $CH_3$ | |
| 1.11 | $CH_3$ | Br | Br | Cl | H | $CF_3$ | $CH_3$ | H | |
| 1.12 | $CH_3$ | Br | Br | Cl | H | $CF_3$ | $CH_3$ | $CH_3$ | |
| 1.13 | $CH_3$ | Br | Cl | Cl | H | $CH_3$ | $CH_3$ | $CH_3$ | White solid (153.4-155.0) |
| 1.14 | $CH_3$ | Br | Br | Cl | H | $CH_3$ | $CH_3$ | H | |
| 1.15 | Cl | Cl | Br | Cl | H | $CH_3$ | $CH_3$ | $CH_3$ | White solid (228.1-229.4) |
| 1.16 | Cl | Cl | Br | Cl | H | $CH_3$ | $CH_3$ | H | |
| 1.17 | Cl | Cl | Br | Cl | Cl | $CH_3$ | $CH_3$ | $CH_3$ | |
| 1.18 | Cl | Cl | $CF_3$ | Cl | H | $CH_2CH_3$ | $CH_3$ | $CH_3$ | |
| 1.19 | Cl | Cl | Br | Cl | H | $CH_2CF_3$ | $CH_3$ | $CH_3$ | |
| 1.20 | Cl | Cl | Br | Cl | Cl | $CH_2CH_2F$ | $CH_3$ | $CH_3$ | |
| 1.21 | Cl | Cl | Br | Cl | Cl | $CH_2CH_2CH_3$ | $CH_3$ | H | |
| 1.22 | Cl | Cl | $CF_3$ | Cl | Cl | $CH_2OCH_3$ | $CH_3$ | $CH_3$ | |
| 1.23 | Cl | Cl | Cl | Cl | H | $CH_3$ | $CH_3$ | $CH_3$ | White solid (209.0-210.2) |
| 1.24 | Cl | CN | Br | Cl | H | $CH_3$ | $CH_3$ | $CH_3$ | White solid (246.6-248.5) |
| 1.25 | Cl | CN | Cl | Cl | H | $CH_3$ | $CH_3$ | $CH_3$ | White solid (248.2-249.4) |
| 1.26 | Cl | CN | Cl | Cl | Cl | $CH_2CH_2OCH_3$ | $CH_3$ | H | |
| 1.27 | Cl | CN | Cl | Cl | H | $CH_2OCH_2CH_3$ | $CH_3$ | H | |
| 1.28 | Cl | Br | Br | Cl | H | $CH_3$ | $CH_3$ | $CH_3$ | White solid (162.5-165.0) |
| 1.29 | Cl | Br | Cl | Cl | H | $CH_3$ | $CH_3$ | $CH_3$ | White solid (229.9-231.4) |
| 1.30 | Cl | F | Br | Cl | H | $CH_3$ | $CH_3$ | $CH_3$ | White solid (284.1-284.3) |
| 1.31 | Cl | F | Cl | Cl | H | $CH_3$ | $CH_3$ | $CH_3$ | |
| 1.32 | Br | Cl | Br | Cl | H | $CH_3$ | $CH_3$ | $CH_3$ | White solid (221.8-222.4) |
| 1.33 | Br | Cl | Cl | Cl | H | $CH_3$ | $CH_3$ | $CH_3$ | White solid (208.8-209.9) |

The present invention also involves an intermediate useful in the direct preparation of the compound of General Formula I, which has a structure of General Formula II:

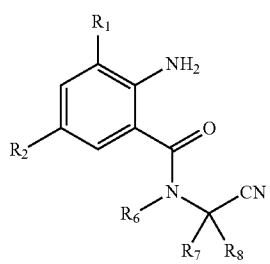

II

In General Formula II:

$R_1$ is selected from halo or $C_1$-$C_3$ alkyl; $R_2$ is selected from halo or CN; $R_6$ is selected from $C_1$-$C_3$ alkyl, $C_1$-$C_3$ haloalkyl or $C_1$-$C_5$ alkoxyalkyl; $R_7$ is selected from $C_1$-$C_5$ alkyl; and $R_8$ is selected from hydrogen or $C_1$-$C_5$ alkyl. The physical properties of some compounds of General Formula II are shown in Table 2.

TABLE 2

The physical properties of some compounds of General Formula II according to the present invention.

| Compound No. | $R_1$ | $R_2$ | $R_6$ | $R_7$ | $R_8$ | Appearance (Melting point (° C.)) |
|---|---|---|---|---|---|---|
| 2.1 | $CH_3$ | Cl | $CH_3$ | $CH_3$ | $CH_3$ | White solid (121.3-123.7) |
| 2.2 | $CH_3$ | Cl | $CH_3$ | $CH_3$ | H | |
| 2.3 | CH3 | Cl | $CH_2OCH_3$ | CH3 | CH3 | |
| 2.4 | CH3 | Cl | $CH_2OCH_3$ | CH3 | H | |
| 2.5 | $CH_3$ | CN | $CH_3$ | $CH_3$ | $CH_3$ | White solid (116.9-118.7) |
| 2.6 | $CH_3$ | CN | $CF_3$ | $CH_3$ | $CH_3$ | |
| 2.7 | $CH_3$ | Br | $CH_3$ | $CH_3$ | $CH_3$ | |
| 2.8 | $CH_3$ | Br | $CF_3$ | $CH_3$ | $CH_3$ | |
| 2.9 | $CH_3$ | Br | $CF_3$ | $CH_3$ | H | |

TABLE 2-continued

The physical properties of some compounds of General Formula II according to the present invention.

| Compound No. | $R_1$ | $R_2$ | $R_6$ | $R_7$ | $R_8$ | Appearance (Melting point (° C.)) |
|---|---|---|---|---|---|---|
| 2.10 | Cl | Cl | $CH_3$ | $CH_3$ | $CH_3$ | Yellow solid (125.3-126.7) |
| 2.11 | Cl | Cl | $CH_2CH_3$ | $CH_3$ | $CH_3$ | |
| 2.12 | Cl | Cl | $CH_2CF_3$ | $CH_3$ | $CH_3$ | |
| 2.13 | Cl | Cl | $CH_2CH_2F$ | $CH_3$ | $CH_3$ | |
| 2.14 | Cl | Cl | $CH_2CH_2CH_3$ | $CH_3$ | H | |
| 2.15 | Cl | Cl | $CH_2OCH_3$ | $CH_3$ | $CH_3$ | |
| 2.16 | Cl | CN | $CH_3$ | $CH_3$ | $CH_3$ | White solid (110.2-110.8) |
| 2.17 | Cl | CN | $CH_2CH_2OCH_3$ | $CH_3$ | H | |
| 2.18 | Cl | Br | $CH_3$ | $CH_3$ | $CH_3$ | Yellow solid (119.7-120.8) |
| 2.19 | Cl | F | $CH_3$ | $CH_3$ | $CH_3$ | Yellow solid (117.8-119.1) |
| 2.20 | Br | Cl | $CH_3$ | $CH_3$ | $CH_3$ | Yellow solid (126.3-126.8) |

Unless otherwise stated, the following terms used in the specification and claims have the meanings discussed below.

"Alkyl" means a saturated aliphatic hydrocarbon group, including linear and branched forms, such as methyl, ethyl, propyl, isopropyl, and the like. "Haloalkyl" means a group in which an alkyl group is substituted with one or more halogen atoms, such as chloroethyl, trifluoromethyl, and the like. "Alkoxy" means a group with an oxygen atom attached to the end of an alkyl group, such as methoxy, ethoxy, and the like.

Hereinafter, a typical preparation method of the present invention is shown, but it is not intended to limit the scope of the present invention in any way.

The compound of General Formula I can be prepared by Reaction Scheme 1, where the substituents are as defined above unless otherwise specified.

Reaction Scheme 1

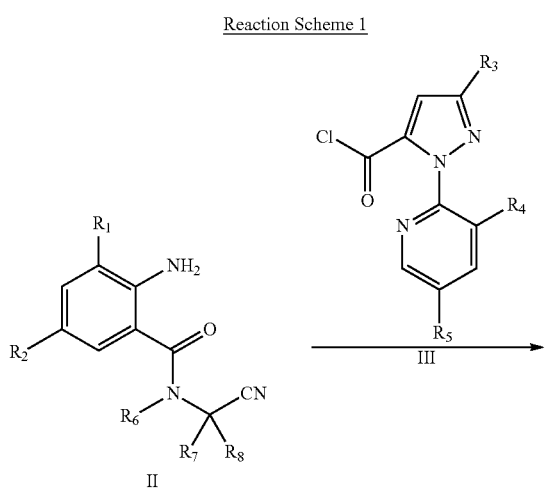

II

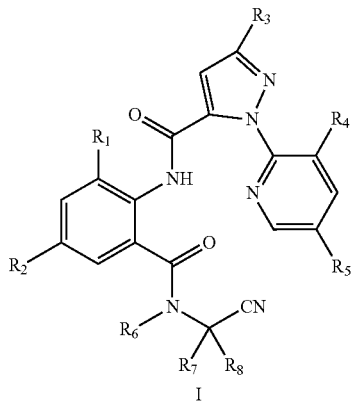

I

The method of Reaction Scheme 1 includes reacting a compound of General Formula II with a compound of General Formula III in the presence or absence of a base to obtain a compound of General Formula I.

The addition of an appropriate amount of a base is beneficial to the reaction. Useful organic bases include: pyridine, triethylamine, potassium tert-butoxide, 4-dimethylaminopyridine or N-methylmorpholine. Useful inorganic bases include: sodium hydride, sodium bicarbonate, sodium carbonate, potassium carbonate, and sodium hydroxide. The reaction is suitably carried out in an inert solvent such as tetrahydrofuran, acetonitrile, toluene, dichloromethane, and the like.

After the reaction is completed, the reaction mixture containing the intended product is separated following a common method, and if necessary, purified by recrystallization or column chromatography, thereby obtaining the intended product. These methods are well documented in literatures, for example, J. Org. Chem. 32, 3069 (1967).

The compound of General Formula II can also be prepared by Reaction Scheme 2, where the substituents are as defined above unless otherwise specified.

Reaction Scheme 2

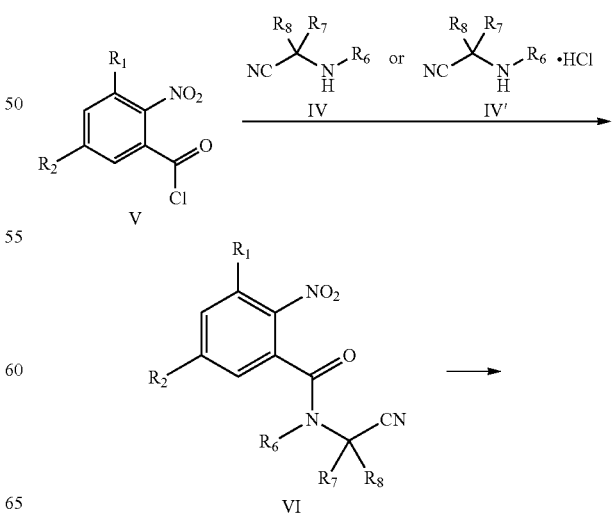

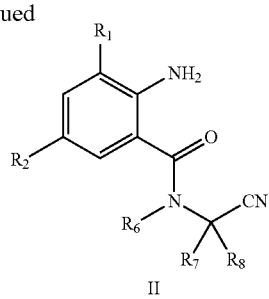

The compound of General Formula V can be prepared by a known general method (for example, Organic Syntheses, 9, 32 (1929)). The compound of General Formula V is prepared with a commercially available chloroformylating reagent such as chlorosulfoxide, and oxalyl chloride.

Some of the compounds of General Formula IV or IV' are commercially available, and some are prepared by a known general method, for example, as described in J. Am. Chem. Soc., 75, 4841-4842(1953), and Chemical Communications, 48(50), 6253-6255(2012).

(1) General Formula V→General Formula VI

The compound of General Formula V is reacted with the compound of General Formula IV to obtain the compound of General Formula VI. A known method, for example, as described in J. Am. Chem. Soc., 135(12), 4628-4631(2013), can be used.

(2) General Formula VI→General Formula II

A typical method includes hydrogenation reduction in a hydroxylic solvent such as ethanol, methanol, and isopropanol in the presence of a metal catalyst such as Pd/C, platinum oxide or Ni (for example, Chinese Journal of Chemical Engineering, 24(9), 1195-1200 (2016)). It can also be prepared by reduction with metals such as zinc powder and iron powder in the presence of an acid catalyst. These methods are generally described in literatures, such as WO 2010042699; and Dye Industry, 37(4): 16-18(2000).

In an organic molecule, the substitution of hydrogen atom(s) with methyl or other alkyl groups can increase the liposolubility solubility of the molecule. It can be known from the analysis of nuclear magnetic data that the introduction of methyl in the present invention has caused changes in the spatial arrangement of molecules. The liposolubility of a molecule is closely related to the conduction of the molecule in plants, insects, and other organisms. Changes in the spatial structure of a molecule also affect the ability of the molecule to bind to the target. These two factors play an important role in the effectiveness of an agent. The effects of the liposolubility and the changes in spatial structure of a molecule on the conductivity and the ability of the bioactive molecule to bind to a target are unpredictable and can be known only after a lot of creative efforts.

It has been found that compared with known benzamidoacetonitrile compounds, the compound of General Formula I of the present invention has unexpectedly high insecticidal activity. Therefore, the present invention also involves use of the compound of General Formula I in controlling pests.

The present invention also involves an insecticidal composition having the compound of General Formula I as an active ingredient. The content in percentage by weight of the active ingredient in the insecticidal composition is between 1-99%. The insecticidal composition also comprises an agriculturally, forestrically, and hygienically acceptable carrier.

The composition of the present invention can be applied in the form of a formulation. The compound of General Formula I, as an active ingredient, can be dissolved or dispersed in a carrier or formulated into a formulation for easier dispersion when used as an insecticide. For example, these chemicals can be made into wettable powders or emulsifiable concentrates. In these compositions, at least one liquid or solid carrier is added, and an appropriate surfactant can be added when needed.

The technical solutions of the present invention also include a method for controlling pests by applying an insecticidal composition of the present invention to the pests or their growth media. Generally, a more suitable effective amount is 10 to 1000 g per hectare.

For some applications, for example, in agriculture, one or more other fungicides, insecticides, herbicides, plant growth regulators or fertilizers may be added to the insecticidal composition of the present invention, thereby bringing about additional advantages and effects.

The present invention has the following advantages. The present invention discloses two types of compounds. Compared with the compounds in the prior art, the compound of General Formula I has a higher activity at a low concentration. Particularly, the compound of the present invention still has 60% or higher of the insecticidal activity at a concentration below 1 ppm. This greatly reduces the amount of the compound used and the residue of the compound in farmland, and is thus environmentally friendly.

The compound of General Formula II is an intermediate for synthesizing the compound of General Formula III. The method of the present invention for synthesizing the compounds of General Formula I and General Formula II has a short process route and a high yield. The present invention provides a new synthesis route for the compound of General Formula I. The present invention solves the problem of inconvenient synthesis of similar compounds in the prior art, greatly reduces the production cost of compounds of General Formula I, is more suitable for industrial applications, and reduces the production cost of manufacturers.

TABLE 3

The test results of some compounds of General Formula I according to the present invention by $^1$HNMR spectroscopy (DMSO-$d_6$, 300 MHz).

| No. | $^1$HNMR data |
| --- | --- |
| 1.1 | 1.50-1.66 (d, 6H), 2.19 (s, 3H), 2.60 (s, 3H), 7.33-7.36 (m, 2H), 7.50 (d, 1H), 7.63 (dd, 1H), 8.20 (dd, 1H), 8.50 (dd, 1H), 10.40 (s, 1H). |
| 1.5 | 1.45 (s, 3H), 1.66 (s, 3H), 2.26 (s, 3H), 2.60 (s, 3H), 7.38 (s, 1H), 7.63 (dd, 1H), 7.82 (d, 1H), 7.91 (d, 1H), 8.20 (dd, 1H), 8.50 (dd, 1H), 10.59 (s, 1H). |
| 1.6 | 1.47 (s, 3H), 1.67 (s, 3H), 2.01 (s, 3H), 2.60 (s, 3H), 7.33 (s, 1H), 7.63 (dd, 1H), 7.82 (d, 1H), 7.91 (d, 1H), 8.20 (dd, 1H), 8.50 (dd, 1H), 10.62 (s, 1H). |
| 1.9 | 1.49-1.67 (d, 6H), 2.19 (s, 3H), 2.60 (s, 3H), 7.35 (s, 1H), 7.46 (d, 1H), 7.61-7.64 (m, 2H), 8.20 (dd, 1H), 8.50 (dd, 1H), 10.38 (s, 1H). |
| 1.14 | 1.49-1.67 (d, 6H), 2.19 (s, 3H), 2.60 (s, 3H), 7.30 (s, 1H), 7.46 (d, 1H), 7.59-7.68 (m, 2H), 8.20 (dd, 1H), 8.50 (dd, 1H), 10.42 (s, 1H). |
| 1.15 | 1.51-1.66 (d, 6H), 2.62 (s, 3H), 7.43 (s, 1H), 7.59 (d, 1H), 7.64 (dd, 1H), 7.88 (d, 1H), 8.20 (dd, 1H), 8.50 (dd, 1H), 10.67 (s, 1H). |
| 1.23 | 1.46-1.67 (d, 6H), 2.61 (s, 3H), 7.37 (s, 1H), 7.60 (d, 1H), 7.63 (dd, 1H), 7.88 (d, 1H), 8.20 (d, 1H), 8.50 (dd, 1H), 10.77 (s, 1H). |

TABLE 3-continued

The test results of some compounds of General Formula I according to the present invention by $^1$HNMR spectroscopy (DMSO-$d_6$, 300 MHz).

| No. | $^1$HNMR data |
|---|---|
| 1.24 | 1.45 (s, 3H), 1.67 (s, 3H), 2.61 (s, 3H), 7.46 (s, 1H), 7.63 (dd, 1H), 8.03 (d, 1H), 8.19 (dd, 1H), 8.32 (d, 1H), 8.50 (dd, 1H), 10.91 (s, 1H). |
| 1.25 | 1.45 (s, 3H), 1.67 (s, 3H), 2.61 (s, 3H), 7.41 (s, 1H), 7.64 (dd, 1H), 8.04 (d, 1H), 8.20 (dd, 1H), 8.32 (d, 1H), 8.50 (dd, 1H), 10.93 (s, 1H). |
| 1.28 | 1.48 (s, 3H), 1.67 (s, 3H), 2.61 (s, 3H), 7.42 (s, 1H), 7.63 (dd, 1H), 7.70 (d, 1H), 7.99 (d, 1H), 8.20 (dd, 1H), 8.50 (dd, 1H), 10.67 (s, 1H). |
| 1.29 | 1.49 (s, 3H), 1.67 (s, 3H), 2.61 (s, 3H), 7.37 (s, 1H), 7.64 (dd, 1H), 7.70 (d, 1H), 7.99 (d, 1H), 8.20 (dd, 1H), 8.50 (dd, 1H), 10.70 (s, 1H). |
| 1.30 | 1.52-1.66 (d, 6H), 2.60 (s, 3H), 7.40-7.43 (m, 2H), 7.63 (dd, 1H), 7.72 (dd, 1H), 8.20 (dd, 1H), 8.50 (dd, 1H), 10.77 (s, 1H). |
| 1.32 | 1.48 (s, 3H), 1.67 (s, 3H), 2.60 (s, 3H), 7.44 (s, 1H), 7.61-7.64 (m, 2H), 8.00 (d, 1H), 8.20 (dd, 1H), 8.51 (dd, 1H), 10.67 (s, 1H). |
| 1.33 | 1.49 (s, 3H), 1.68 (s, 3H), 2.60 (s, 3H), 7.38 (s, 1H), 7.61-7.65 (m, 2H), 8.00 (d, 1H), 8.20 (dd, 1H), 8.51 (dd, 1H), 10.69 (s, 1H). |
| 2.10 | 1.74 (s, 6H), 2.85 (s, 3H), 5.52 (s, 2H), 7.22 (d, 1H), 7.50 (d, 1H). |
| 2.16 | 1.74 (s, 6H), 2.84 (s, 3H), 6.39 (s, 2H), 7.64 (d, 1H), 7.88 (d, 1H). |
| 2.18 | 1.78 (s, 6H), 2.85 (s, 3H), 5.55 (s, 2H), 7.31 (d, 1H), 7.58 (d, 1H). |
| 2.19 | 1.74 (s, 6H), 2.85 (s, 3H), 5.23 (s, 2H), 7.10 (dd, 1H), 7.41 (dd, 1H). |
| 2.20 | 1.74 (s, 6H), 2.85 (s, 3H), 5.44 (s, 2H), 7.27 (d, 1H), 7.63 (d, 1H). |

DETAILED DESCRIPTION OF THE EMBODIMENTS

The present invention is further described in detail below with reference to specific embodiments, but the embodiments are not intended to limit the present invention.

Example 1

Compound 1.15: Synthesis of N-(6-N-((2-cyanopropan-2-yl)-N-methylcarbamoyl)-2,4-dichlorophenyl)-1-(3-chloropyridin-2-yl)-3-bromo-1H-pyrazol-5-carboxamide (1) Synthesis of 2-methyl-2-(methylamino)propionitrile

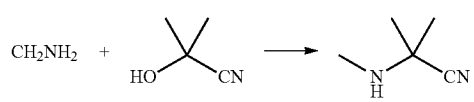

Acetone cyanohydrin (8.5 g, 0.1 mol) was added to a 50 ml four-necked flask, and then methylamine gas (3.1 g, 0.1 mol) was slowly introduced at room temperature. After that, the reaction was continuously stirred at room temperature for 5 h, and extracted with dichloromethane (10 ml×3). The organic phase were combined and dried over anhydrous sodium sulfate. Then, the solvent was removed under reduced pressure to obtain a colorless transparent liquid (6.18 g, yield 63.0%).

(2) Synthesis of 2-nitrobenzoyl chloride

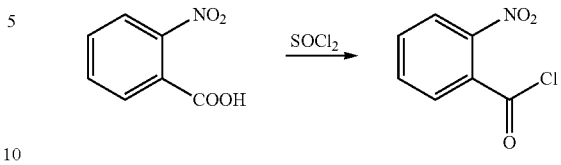

2-nitrobenzoic acid (8.4 g, 0.05 mol), dichloroethane (100 ml), chlorosulfoxide (17.8 g, 0.15 mol), and DMF (1 drop) were sequentially added to a 250 ml single-necked flask, heated to reflux and reacted for 3 h. Then, the solvent was removed under reduced pressure to obtain a yellow liquid (8.9 g, yield 95.9%). The product was directly used in next step without further post-treatment.

(3) Synthesis of 2-nitro-N-methyl-N-(2-cyanopropan-2-yl)benzamide

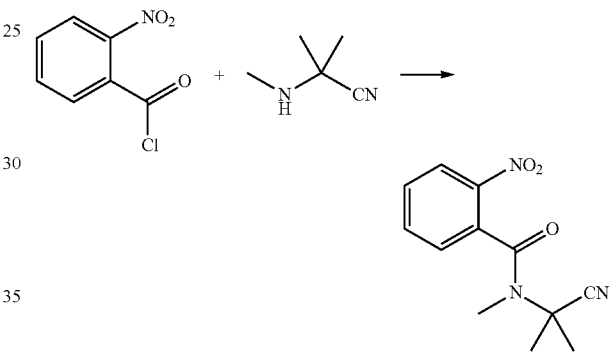

2-methyl-2-(methylamino)propionitrile (4.9 g, 0.05 mol), dichloromethane (20 ml), and triethyl amine (5.1 g, 0.05 mol) were sequentially added to a 250 ml four-necked flask. Then 2-nitrobenzoyl chloride (8.9 g, 0.048 mol) in dichloromethane (20 ml) was added dropwise at 0° C., and then continuously reacted for 2 h with stirring at 0° C. The reaction solution was added with water (50 ml), and extracted with dichloromethane (20 ml×3). The organic phases were combined, washed with saturated aqueous sodium chloride solution, and dried over anhydrous sodium sulfate. The solvent was removed under reduced pressure to obtain a yellow solid (9.1 g, yield 76.6%).

(4) Synthesis of 2-amino-N-methyl-N-(2-cyanopropan-2-yl)benzamide

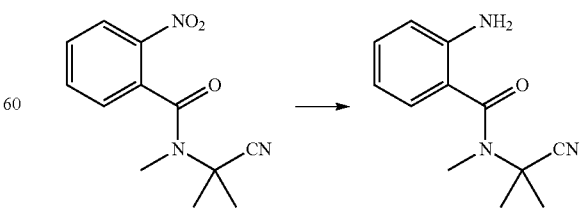

Water (20 ml), reduced Fe powder (2.2 g, 0.04 mol), and 30% hydrochloric acid (1 ml) were sequentially added to a 100 ml four-necked flask, slowly heated to 80° C., and stirred for 30 min at 80° C. Then, 2-nitro-N-methyl-N-(2-cyanopropan-2-yl)benzamide (2.5 g, 0.01 mol) was added batchwise, while the temperature was maintained at no more than 80° C. After that, the reaction was continuously stirred at 80° C., until the reaction was completed as indicated by HPLC. The reaction solution was cooled to room temperature, added with sodium hydroxide (1.6 g), and filtered with suction. The filter cake was washed with hot water, and the collected filtrate was extracted with ethyl acetate (2×100 ml). The organic phase was washed with water, saturated sodium carbonate solution and saturated brine, and dried over anhydrous sodium sulfate. The solvent was removed under reduced pressure to obtain a brown liquid (1.37 g, yield 63.3%).

(5) Synthesis of N-(1-cyanoisopropyl)-N-methyl-2-amino-3,-5-dichlorobenzamide

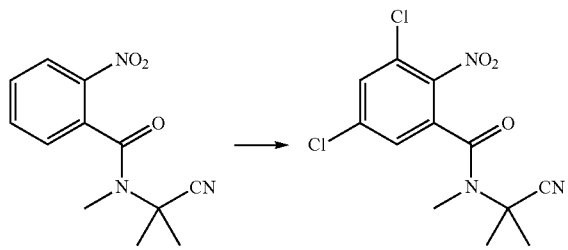 [SMILES: CN(C(=O)c1ccccc1[N+](=O)[O-])C(C)(C)C#N ; CN(C(=O)c1cc(Cl)cc(Cl)c1[N+](=O)[O-])C(C)(C)C#N]

2-amino-N-methyl-N-(2-cyanopropan-2-yl)benzamide (1.1 g, 5 mmol), N-chlorosuccinimide (2.2 g, 12.5 mmol) and DMF (20 ml) were sequentially added to a 100 ml four-necked flask, and reacted with stirring at room temperature until the reaction was completed as indicated by HPLC. The reaction solution was poured into water (100 ml), and extracted with ethyl acetate (20 ml×3). The organic phases were combined, washed with saturated aqueous sodium chloride solution, and dried over anhydrous sodium sulfate. The solvent was removed under reduced pressure to obtain a light yellow solid (1.1 g, yield 78.6%).

(6) Synthesis of N-(6-N-((2-cyanopropan-2-yl)-N-methylcarbamoyl)-2,4-dichlorophenyl)-1-(3-chloro-pyridin-2-yl)-3-bromo-1H-pyrazol-5-carboxamide

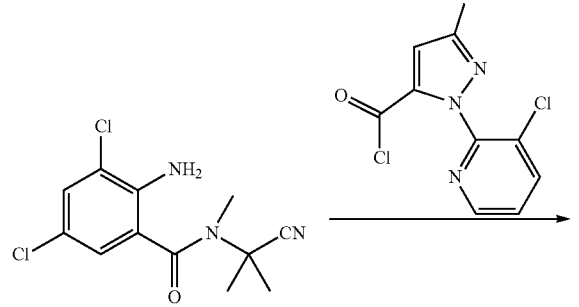

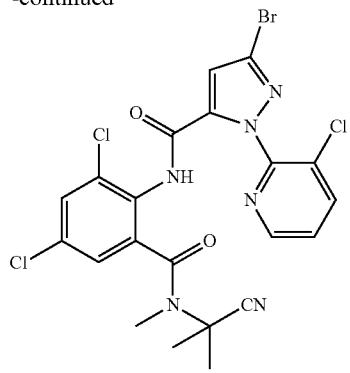

2-amino-3,5-dichloro-N-methyl-N-(2-cyanopropan-2-yl)benzamide (1 g, 0.00376 mol), tetrahydrofuran (10 ml), and pyridine (0.3 g, 0.00376 mol) were sequentially added to a 50 ml four-necked flask. 2-(3-chloro-pyridin-2-yl)-5-bromo-2H-pyrazol-3-carbonyl chloride (1.2 g, 0.00376 mol) (prepared according to a method as described in WO 02/070483) in tetrahydrofuran (10 ml) was added dropwise in an ice bath. The reaction was stirred overnight in an ice bath, during which the progress of the reaction was traced by HPLC. The reaction solution was poured into water (50 ml), and extracted with dichloromethane (3×20 ml). The organic phase was washed sequentially with saturated sodium carbonate solution, saturated aqueous sodium chloride solution and water, and dried over anhydrous sodium sulfate. The solvent was removed under reduced pressure, and the resulting crude product was purified by column chromatography (eluent: ethyl acetate:petroleum ether=3:1), to obtain a white solid (0.85 g, yield 41.9%).

Example 2

Compound 1.1: Synthesis of N-(2-N-((2-cyanopropan-2-yl)-N-methylcarbamoyl)-4-chloro-6-methylphenyl)-1-(3-chloropyridin-2-yl)-3-bromo-1H-pyrazol-5-carboxamide (1) Synthesis of 2-nitro-3-methylbenzoyl chloride

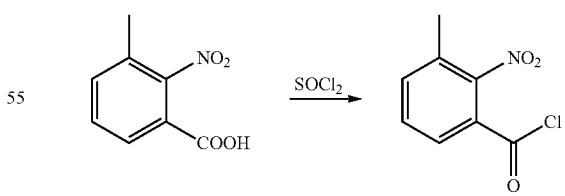

2-nitro-3-methylbenzoic acid (5.4 g, 0.03 mol), dichloroethane (100 ml), chlorosulfoxide (23.8 g, 0.2 mol), and DMF (1 drop) were sequentially added to a 250 ml single-necked flask, heated to reflux and reacted for 3 h. Then, the solvent was removed under elevated pressure to obtain a brown liquid (5.7 g, yield 95.2%). The product was directly used in next step without further post-treatment.

(2) Synthesis of N-(1-cyanoisopropyl)-N-methyl-3-methyl-2-nitrobenzamide

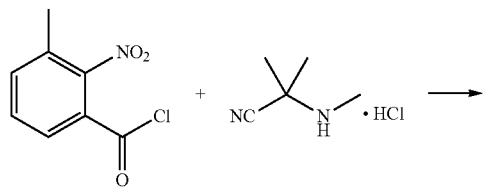

2-methyl-2-(methylamino)propionitrile hydrochloride (4.0 g, 0.03 mol), tetrahydrofuran (10 ml), water (10 ml), and NaHCO$_3$ (5.1 g, 0.06 mol) were sequentially added to a 250 ml four-necked flask. 2-nitro-3-methylbenzoyl chloride (5.7 g) in tetrahydrofuran (20 ml) was added dropwise at −10° C., and then continuously reacted for 2 h with stirring at −10° C. The reaction solution was added with water (50 ml), and extracted with ethyl acetate (20 ml×3). The organic phases were combined, washed with saturated aqueous sodium chloride solution, and dried over anhydrous sodium sulfate. The solvent was removed under reduced pressure to obtain a brown solid (4.4 g, yield 56.5%).

(3) Synthesis of N-(1-cyanoisopropyl)-N-methyl-3-methyl-2-aminobenzamide

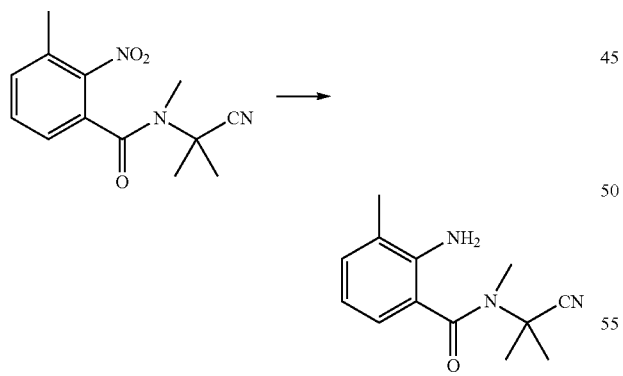

Water (20 ml), reduced Fe powder (2.2 g, 0.04 mol), and 30% hydrochloric acid (1 ml) were sequentially added to a 100 ml four-necked flask, slowly heated to 80° C. and stirred for 30 min at 80° C. Then, N-(1-cyanoisopropyl)-N-methyl-3-methyl-2-nitrobenzamide (2.6 g, 0.01 mol) was added batchwise, while the temperature was maintained at no more than 80° C. After that, the reaction was continuously stirred at 80° C., until the reaction was completed as indicated by HPLC. The reaction solution was cooled to room temperature, added with sodium hydroxide (1.6 g), and filtered with suction. The filter cake was washed with hot water, and the collected filtrate was extracted with ethyl acetate (2×100 ml). The organic phase was washed with water, saturated sodium carbonate solution and saturated brine, and dried over anhydrous sodium sulfate. The solvent was removed under reduced pressure to obtain a brown solid (1.68 g, yield 71.3%).

(4) Synthesis of N-(1-cyanoisopropyl)-N-methyl-2-amino-3-methyl-5-chlorobenzamide

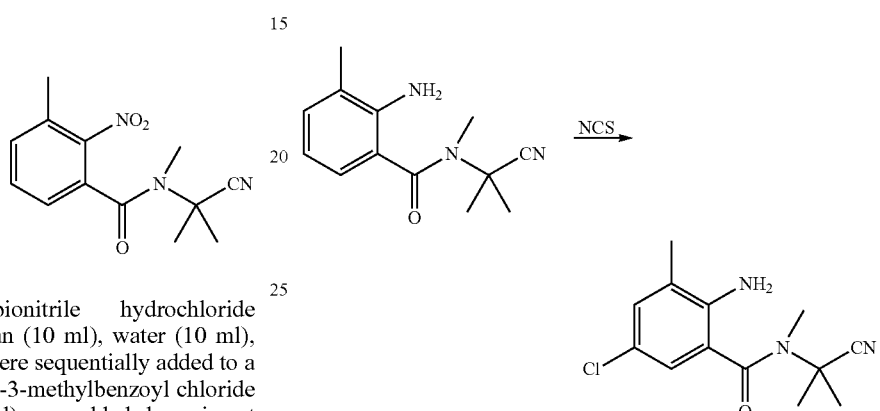

N-(1-cyanoisopropyl)-N-methyl-3-methyl-2-aminobenzamide (1.6 g, 6.9 mmol), N-chlorosuccinimide (1.4 g, 10.3 mmol) and DMF (20 ml) were sequentially added to a 100 ml four-necked flask, and reacted with stirring at room temperature until the reaction was completed as indicated by HPLC. The reaction solution was poured into water (100 ml), and extracted with ethyl acetate (20 ml×3). The organic phases were combined, washed sequentially with saturated aqueous sodium chloride solution and water, and dried over anhydrous sodium sulfate. The solvent was removed under reduced pressure to obtain a light yellow solid (1.52 g, yield 83.1%).

(5) Synthesis of N-(2-N-((2-cyanopropan-2-yl)-N-methylcarbamoyl)-4-chloro-6-methylphenyl)-1-(3-chloropyridin-2-yl)-3-bromo-1H-pyrazol-5-carboxamide

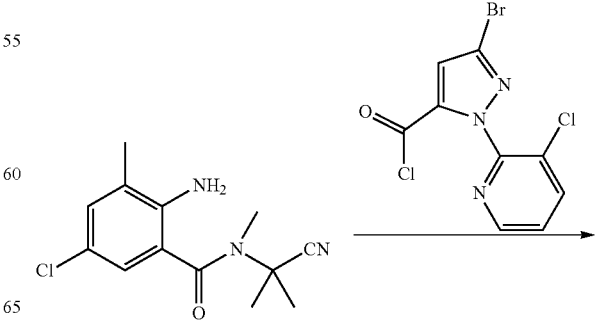

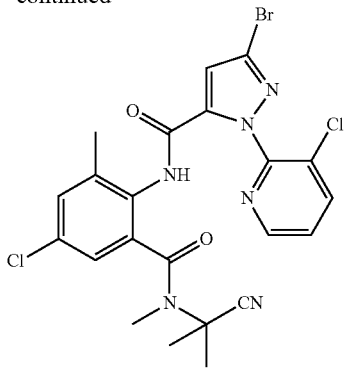

N-(1-cyanoisopropyl)-N-methyl-2-amino-3-methyl-5-chlorobenzamide (0.3 g, 1 mmol), dichloromethane (10 ml), triethyl amine (0.1 g, 1 mmol), and 2-(3-chloro-pyridin-2-yl)-5-bromo-2H-pyrazol-3-carbonyl chloride (0.32 g, 1 mmol) (prepared according to a method as described in WO 02/070483) were sequentially added to a 50 ml single-necked flask, and stirred at room temperature, until the reaction was completed as indicated by HPLC. The reaction solution was poured into water (50 ml), and extracted with dichloromethane (3×20 ml). The organic phase was washed sequentially with saturated sodium carbonate solution, saturated aqueous sodium chloride solution and water, and dried over anhydrous sodium sulfate. The solvent was removed under reduced pressure, and the resulting crude product was purified by column chromatography (eluent:ethyl acetate:petroleum ether=3:1), to obtain a white solid (0.20 g, yield 36.1%).

Example 3

Compound 1.6: Synthesis of N-(2-N-((2-cyanopropan-2-yl)-N-methylcarbamoyl)-4-cyano-6-methylphenyl)-1-(3-chloropyridin-2-yl)-3-chloro-1H-pyrazol-5-carboxamide (1) Synthesis of 2-amino-3-methyl-5-iodo-N-(1-cyanoisopropyl)-N-methylbenzamide

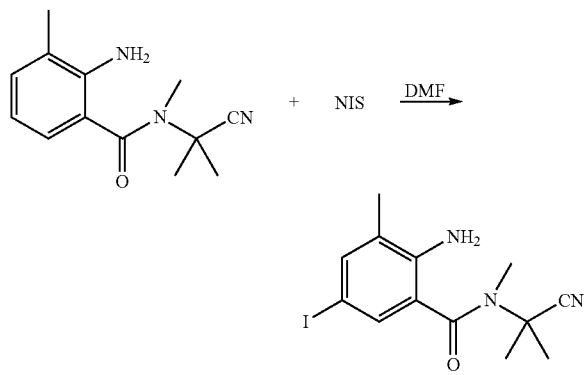

N-(1-cyanoisopropyl)-N-methyl-3-methyl-2-aminobenzamide (76.3 g, 0.33 mol) and DMF (250 ml) were sequentially added to a 500 ml four-necked flask. N-chlorosuccinimide (78.2 g, 0.35 mol) was slowly added with stirring at room temperature, heated to 75° C., and reacted until the reaction was completed as indicated by HPLC. The reaction solution was poured into water (500 ml), and a large amount of solid was precipitated, which was filtered with suction, and dried to obtain a light purple powdered solid (69.1 g, yield 58.6%).

(2) Synthesis of 2-amino-3-methyl-5-cyanobenzoic Acid

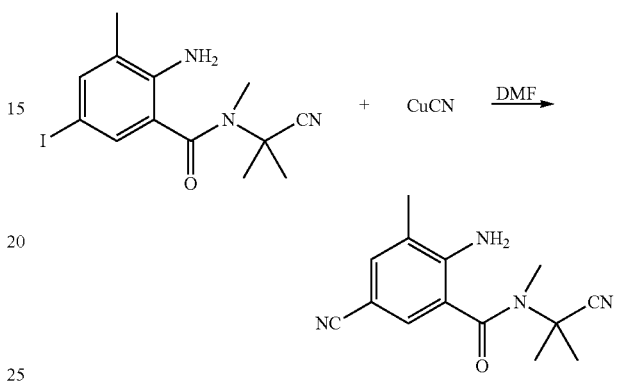

2-amino-3-methyl-5-iodo-N-(1-cyanopropyl)-N-methylbenzamide (60 g, 0.17 mol), CuCN (33 g, 0.37 mol) and DMF (300 ml) were sequentially added to a 500 ml four-necked flask, heated to 145° C., and reacted until the reaction was completed as indicated by HPLC. After most of the solvent was removed, water (720 ml) and ethylenediamine (15.8 g) were added. The insoluble material was removed by filtration with suction, and then 30% hydrochloric acid (64 g) was slowly added to the filtrate to adjust the pH to weakly acidic. A large amount of a white solid was precipitated, and filtered with suction. The filter cake was dried to obtain a white solid (18.8 g, yield 43.2%).

(3) Synthesis of 3-chloro-2-pyridinylhydrazine

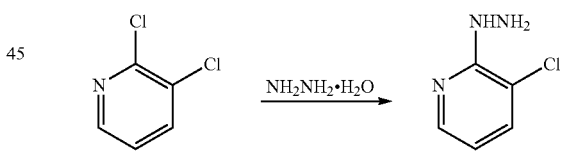

2,3-dichloropyridine (185 g, 1.25 mol) was added to n-butanol (800 mL), and then hydrazine hydrate (315 g) was added, heated to reflux, and reacted for 35-40 h. The reaction solution was cooled to room temperature, filtered, and dried to obtain a white crystal (120 g, yield 66.9%).

(4) Synthesis of ethyl 2-(3-chloro-2-pyridyl)-5-carbonylpyrazolon-3-carboxylate

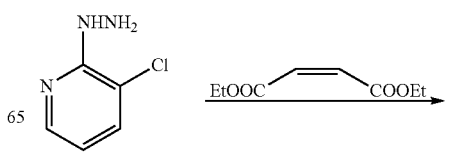

-continued

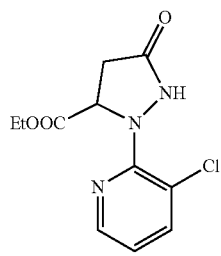

Chopped sodium lumps (24 g, 1.04 mol) were added to absolute ethanol (920 g) in portions and warmed to reflux naturally. After the sodium was completely dissolved, the solution was cooled to below 40° C., and 3-chloro-2-pyridinylhydrazine (120 g, 0.836 mol) was added at a time. Diethyl maleate (210 g, 1.22 mol) was added dropwise over 1 h while the temperature was maintained at 40-45° C. The reaction was continued for 4 h while the temperature was maintained at 40-45° C. Then, the reaction solution was cooled to room temperature, and poured into glacial acetic acid in cold water batchwise with stirring. Ethanol (650-700 mL) was distilled off under reduced pressure, and then the solution was cooled to room temperature, stood, and filtered. The filter cake was washed with ethanol (65 mL×2), collected, and dried to obtain a finished product (120 g). The filtrate and washings were combined, and concentrated under reduced pressure to remove almost all ethanol and obtain a large amount of a dark green solution with black solid. The solution was extracted with chloroform (200 mL), dried over anhydrous magnesium sulfate, filtered, and concentrated to dryness. Toluene (50 mL) was added, and heated to obtain a uniform solution. The solution was cooled to room temperature, frozen in a refrigerator overnight, filtered, washed with toluene (15 mL), and dried to obtain a dark green solid (9 g, total yield 57.2%).

(5) Synthesis of ethyl 3-chloro-1-(3-chloro-2-pyridyl)-4,5-dihydropyrazol-5-carboxylate

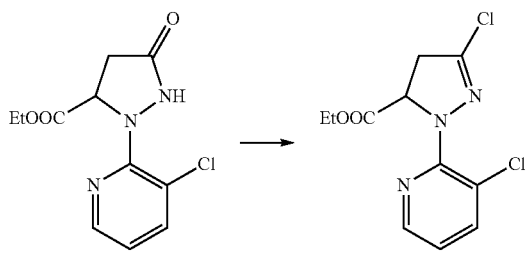 [SMILES: CCOC(=O)C1CC(=O)NN1c1ncccc1Cl ; CCOC(=O)C1CC(Cl)=NN1c1ncccc1Cl]

Phosphorus oxychloride (109.8 g, 0.716 mol) was added to acetonitrile (430 g), and then ethyl 2-(3-chloro-2-pyridyl)-5-carbonylpyrazolon-3-carboxylate (134.5 g, 0.499 mol) was added. The mixture was heated to reflux and reacted for 4-5 h. Then the reaction solution was poured into iced water (1200 g), extracted twice with chloroform (400 mL), and washed once with 10% aqueous sodium bicarbonate solution (300 mL). The organic phase was separated, dried over anhydrous sodium sulfate for 5 h, filtered, and concentrated to almost dryness under reduced pressure. Absolute ethanol (200 mL) was added, heated to 60° C., and stirred evenly. The reaction solution was removed while hot, frozen overnight at −18° C., filtered, washed with anhydrous ethanol, and dried to obtain a light purple crystal (113.7 g, yield 79.1%).

(6) Synthesis of ethyl 3-chloro-1-(3-chloro-2-pyridyl)-pyrazol-5-carboxylate

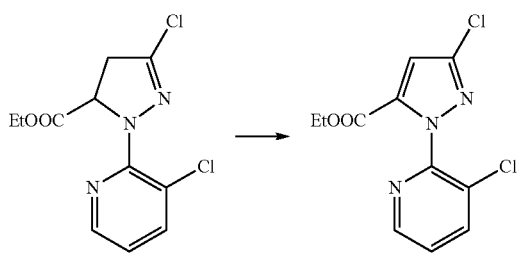 [SMILES: CCOC(=O)C1CC(Cl)=NN1c1ncccc1Cl ; CCOC(=O)c1cc(Cl)nn1-c1ncccc1Cl]

Ethyl 3-chloro-1-(3-chloro-2-pyridyl)-4,5-dihydropyrazol-5-carboxylate (110.1 g, 0.382 mol) was added to acetonitrile (910 mL), and stirred until dissolved. Concentrated Sulfuric acid (65.1 g, 0.664 mol) and then potassium persulfate (181 g, 0.67 mol) were added. The mixture was heated to reflux, and reacted for 15 h under reflux with stirring. After cooling, the reaction solution was poured into iced water (1500 g), extracted twice with chloroform (500 mL), washed with 10% sodium bicarbonate (100 mL), dried over anhydrous magnesium sulfate, filtered, and concentrated to dryness under reduced pressure to obtain a light yellow solid (85.8 g, yield 76.5%).

(7) Synthesis of 3-chloro-1-(3-chloro-2-pyridyl)-pyrazol-5-carboxylic Acid

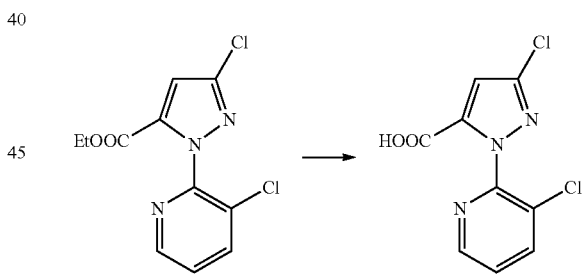

(57.2 g, 0.2 mol) was suspended in ethanol (850 g), and heated to 50° C. Then potassium hydroxide (28.6 g, 0.511 mol) in water (250 mL) was added dropwise over 30 min. The reaction was continued at 50-55° C. for 5 h. All the ethanol was removed by concentration under reduced pressure, and then water (300 mL) was added. After cooling to room temperature, and the solution was extracted with ethyl acetate (100 mL). The aqueous phase was distilled under reduced pressure to remove the residual ethyl acetate, and cooled to room temperature. 15% hydrochloric acid was slowly added dropwise with stirring until the pH of the solution was 2. The solution was continuously stirred for 2 h, filtered, washed with water, and dried to obtain a light yellow solid (46.1 g, yield 89.3%).

(10) Synthesis of 3-bromo-1-(3-chloro-2-pyridyl)-pyrazol-5-formyl chloride

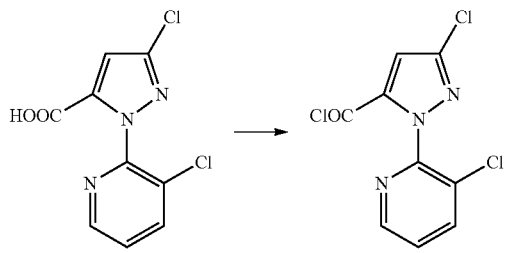

3-chloro-1-(3-chloro-2-pyridyl)-pyrazol-5-carboxylic acid (30 g, 0.33 mol) was suspended in dichloromethane (1500 mL), and then DMF (1 mL) was added. After about 4 h, oxalyl chloride (63 g, 0.496 mol) was added dropwise to the above suspension, and reacted overnight with stirring to obtain a clear solution. The solution was concentrated to dryness under reduced pressure to obtain a semi-solid, which was sealed for use.

(11) Synthesis of N-(2-N-((2-cyanopropan-2-yl)-N-methylcarbamoyl)-4-cyano-6-methylphenyl)-1-(3-chloropyridin-2-yl)-3-chloro-1H-pyrazol-5-carboxamide

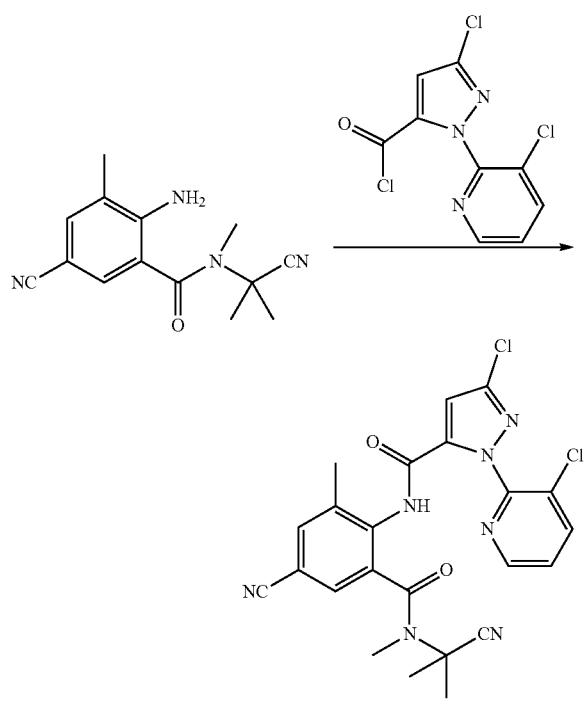

N-(1-cyanoisopropyl)-N-methyl-3-methyl-2-amino-5-cyanobenzamide (0.26 g, 1 mmol), acetonitrile (10 ml), and triethylamine (0.1 g, 1 mmol) were sequentially added to a 50 ml single-necked flask, and heated to reflux. At the reflux temperature, 2-(3-chloro-pyridin-2-yl)-5-chloro-2H-pyrazol-3-carbonyl chloride (0.28 g, 1 mmol) in acetonitrile (2 ml) was added at a time and continuously reacted under reflux with stirring, until the reaction was completed as indicated by HPLC. The reaction solution was poured into water (50 ml), and extracted with dichloromethane (3×20 ml). The organic phase was washed sequentially with saturated sodium carbonate solution, saturated aqueous sodium chloride solution and water, and dried over anhydrous sodium sulfate. The solvent was removed under reduced pressure, and the resulting crude product was purified by column chromatography (eluent: ethyl acetate:petroleum ether=3:1), to obtain a white solid (0.28 g, yield 56.7%).

Biological Activity Test

The test reagents were all dissolved in a mixed solvent of acetone:N'N'-dimethylcarboxamide (1:1) to give a 1000 mg/L solution. 1% Tween-80 was added as an emulsifier to each solution. These solutions were then diluted with 1% Tween-20 solution in water to give desired concentrations of test solutions. An aqueous solution containing 1% Tween-20 was used as a control.

Example 4: Insecticidal Effect on *Spodoptera exigua*

The cabbage leaves were punched into leaf discs with a diameter of 1 cm, and sprayed with Airbrush. A certain concentration of the test compound was sprayed on both the front and back sides of each leaf disc in a volume of 0.5 ml. After drying in the shade, for each treatment, 10 test insects (3rd instar larvae) were inoculated, and 3 replicates were set. After treatment, they were cultivated in a chamber at 25° C. with a relative humidity of 60% to 70% in the dark. After 120 h, the number of surviving insects was investigated to calculate the mortality.

When the concentration of the reagent solution is 10 ppm, some compounds such as 1.1, 1.15, 1.23, 1.32 and 1.33 have a better control effect on *Spodoptera exigua*, reaching more than 80%.

Example 5: Insecticidal Effect on *Spodoptera litura*

The cabbage leaves that had not been exposed to insecticides were cut into leaf discs of about 40 square-mm with scissors. The leaf discs were immersed in each compound solution for 30 s. Then the leaf discs were placed on absorbent paper and air-dried until there were no obvious water stains on the leaf discs. The leaf discs soaked with the reagents were placed in a petri dish (7 cm), each petri dish having 3 leaf discs. The 3rd instar larvae of *Spodoptera litura* raised on the indoor cabbage plants were gently picked up with a pen brush and placed on the leaf discs in the petri dish, each petri dish having 10-15 insects. After the insects were inoculated, the petri dish was covered, and placed in an insect-cultivating chamber at 25° C. with a 16-h-light/8-h-dark photoperiod. After 120 h, the number of surviving insects was investigated to calculate the mortality.

Some test results are as follows:

When the concentration of the reagent solution is 4 ppm, the mortality of 3rd instar larvae of *Spodoptera litura* caused by some compounds such as 1.1, 1.9, 1.15, 1.23, 1.32 and 1.33 is 80% or higher.

When the concentration of the reagent solution is 1 ppm, the mortality of 3rd instar larvae of *Spodoptera litura* caused by some compounds such as 1.1, 1.9, 1.15, and 1.23 is 80% or higher.

Example 6: Insecticidal Effect on *Helicoverpa armigera*

The prepared fresh cabbage leaf discs were immersed in a certain concentration of test compound solution for 10 sec, removed and dried naturally. A 24-well plate was used, one treated leaf discs was placed in each well, and one third-instar larvae of *Helicoverpa armigera* was inoculated and maintained moisturized. After 120 h, the number of surviving insects was investigated to calculate the mortality.

Some test results are as follows:

When the concentration of the reagent solution is 4 ppm, the mortality of 3rd instar larvae of *Helicoverpa armigera* caused by some compounds such as 1.1, 1.15, 1.32, and 1.33 is 80% or higher.

When the concentration of the reagent solution is 1 ppm, the mortality of 3rd instar larvae of *Helicoverpa armigera* caused by some compounds such as 1.1, 1.5, 1.15, and 1.33 is 80% or higher.

Example 7: Insecticidal Effect on *Cnaphalocrocis medinalis*

The rice seedlings that had not been exposed to insecticides were pulled out, and the soil was washed off from the root. After there were no obvious water stains on the leaf discs, the stems and leaves of the seedlings were immersed in different concentrations of reagent solutions (where the reagent solution was contained in a test tube, and the stem and leaves were immersed downward into it). After immersing for 30 s, they were taken out, placed on absorbent paper, and air dried until there were no water stains on the leaves. The filter paper was laid in a petri dish (7 cm), and moistened with clean water. The petri dish was inverted until no water drops flowed out. The leaves were cut from the treated seedlings into leaf segments having substantially the same diameter as the petri dish. The leaf segments were spread on the filter paper in the petri dish, each petri dish having 15-20 leaf segments.

The 3rd-4th instar larvae of *Cnaphalocrocis medinalis* raised on the indoor wheat plant were gently picked up with a pen brush and placed on the leaf segments in the petri dish, each petri dish having 10 insects. After the insects were inoculated, the petri dish was covered, and placed in an insect-cultivating chamber at 25° C. with a 16-h-light/8-h-dark photoperiod. The death of *Cnaphalocrocis medinalis* was investigated 72 h after the insects were inoculated.

Some test results are as follows:

When the concentration of the reagent solution is 20 ppm, the mortality of 3rd-4th instar larvae of *Cnaphalocrocis medinalis* caused by some compounds such as 1.1, 1.9, 1.15, 1.23, 1.32 and 1.33 is 80% or higher.

When the concentration of the reagent solution is 10 ppm, the mortality of 3rd-4th instar larvae of *Cnaphalocrocis medinalis* caused by some compounds such as 1.1, 1.15, and 1.32 is 80% or higher.

Example 8: Insecticidal Effect on *Plutella xylostella*

Third instar larvae of *Plutella xylostella* were used. Cabbages were washed, air dried, punched into leaf discs, immersed in reagent solutions for 10 sec, taken out, naturally dried and then placed in a Petri dish. 10 third-instar larvae of *Plutella xylostella* were inoculated to each Petri dish, and three replicates were set. The number of deaths in 3 days was investigated, and the mortality was calculated.

Some test results are as follows:

When the concentration of the reagent solution is 1 ppm, the mortality of *Plutella xylostella* caused by some compounds such as 1.1, 1.9, 1.15, 1.23, 1.24, 1.28-1.30, 1.32 and 1.33 is 90% or higher.

According to the above method, Comparative Compounds KC1 (Compound 1.14 in WO 2008134969) and KC2 (Compound 1.18 in WO 2008134969) in the prior art which are closest in structure to the compound of the present invention were tested for the insecticidal activity on *Plutella xylostella*. The experimental results are shown in Table 4 below.

TABLE 4

Parallel comparison of the insecticidal activity of Compound 1.15 of the present invention with known Compound KC1 and KC2 on *Plutella xylostella* (mortality %)

| Insecticidal activity | Concentration ppm | | |
| --- | --- | --- | --- |
| Compound | 0.5 | 0.05 | 0.01 |
| 1.15 | 100 | 86.67 | 66.67 |
| KC1 | 71.88 | 45.71 | |
| KC2 | 88.24 | 51.43 | 28.13 |

It can be seen from the data in the above table that when used in the killing of *Plutella xylostella*, compared with Compound KC1 and Compound KC2 disclosed in the prior art, the compound of the present invention still has higher activity at a concentration of less than 1 ppm. Compared with the test results of KC1 and KC2, the compound of the present invention has a lower dosage, but a higher activity.

The structural formula of KC2 is as follows:

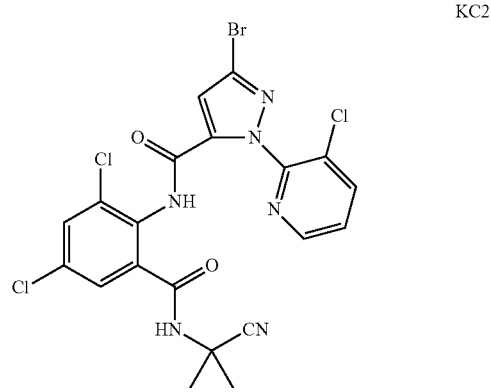 [SMILES: CC(C)(C#N)NC(=O)c1cc(Cl)cc(Cl)c1NC(=O)c1cc(Br)nn1-c1ncccc1Cl]

What is claimed is:

1. An N-alkyl-N-cyanoalkylbenzamide compound of General Formula

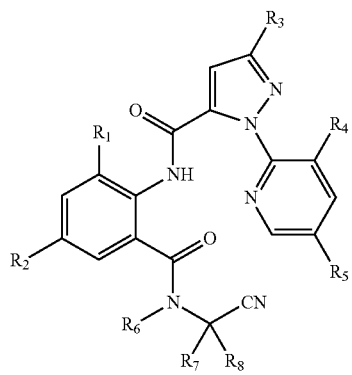

I wherein
- $R_1$ is selected from halo or $C_1$-$C_3$ alkyl;
- $R_2$ is selected from halo or CN;
- $R_3$ is selected from halo, $C_1$-$C_3$ haloalkyl;
- $R_4$ is selected from halo;
- $R_5$ is selected from H or halo;
- $R_6$ is selected from $C_1$-$C_3$ alkyl, $C_1$-$C_3$ haloalkyl or $C_1$-$C_5$ alkoxyalkyl;
- $R_7$ is selected from $C_1$-$C_5$ alkyl; and
- $R_8$ is selected from hydrogen or $C_1$-$C_5$ alkyl,
- wherein the compound has an insecticidal activity of at least 90% when in a composition at 0.5 ppm concentration.

2. The N-alkyl-N-cyanoalkylbenzamide compound according to claim 1, wherein
- $R_1$ is selected from chloro, bromo or methyl;
- $R_2$ is selected from chloro, bromo, fluoro or CN;
- $R_3$ is selected from chloro, bromo or trifluoromethyl;
- $R_4$ is selected from chloro;
- $R_5$ is selected from H or chloro;
- $R_6$ is selected from $C_1$-$C_3$ alkyl, $CH_2OCH_3$, $CH_2OCH_2CH_3$, $CH_2CH_2OCH_3$, $CF_3$, $CH_2CH_2F$, $CH_2CHF_2$, $CH_2CF_3$, $CF_2CF_3$ or $CF(CF_3)_2$;
- $R_7$ is selected from methyl; and
- $R_8$ is selected from hydrogen or methyl.

3. The N-alkyl-N-cyanoalkylbenzamide compound according to claim 1, wherein
- $R_1$ is selected from chloro, bromo or methyl;
- $R_2$ is selected from chloro, bromo, fluoro or CN;
- $R_3$ is selected from chloro or bromo;
- $R_4$ is selected from chloro;
- $R_5$ is selected from H;
- $R_6$ is selected from methyl;
- $R_7$ is selected from methyl; and
- $R_8$ is selected from methyl.

4. An intermediate compound for preparing an N-alkyl-N-cyanoalkylbenzamide compound, wherein the intermediate compound is represented by General Formula II:

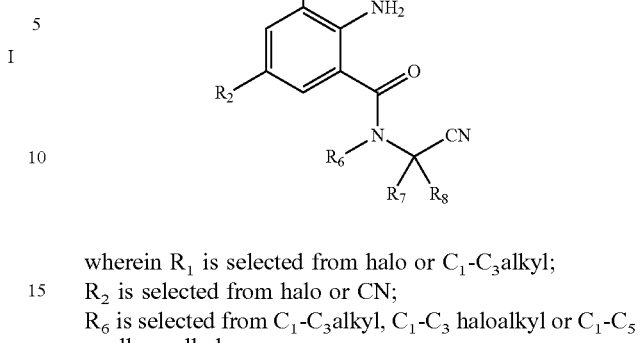

wherein $R_1$ is selected from halo or $C_1$-$C_3$ alkyl;
- $R_2$ is selected from halo or CN;
- $R_6$ is selected from $C_1$-$C_3$ alkyl, $C_1$-$C_3$ haloalkyl or $C_1$-$C_5$ alkoxyalkyl;
- $R_7$ is selected from $C_1$-$C_5$ alkyl; and
- $R_8$ is selected from hydrogen or $C_1$-$C_5$ alkyl.

5. A method for preparing an N-alkyl-N-cyanoalkylbenzamide compound of General Formula I with the compound of General Formula II according to claim 4, comprising:
reacting a compound of General Formula II with a compound of General Formula III to obtain a compound of General Formula I, wherein chemical formula of General Formula I, II, and III and the reaction scheme are shown below:

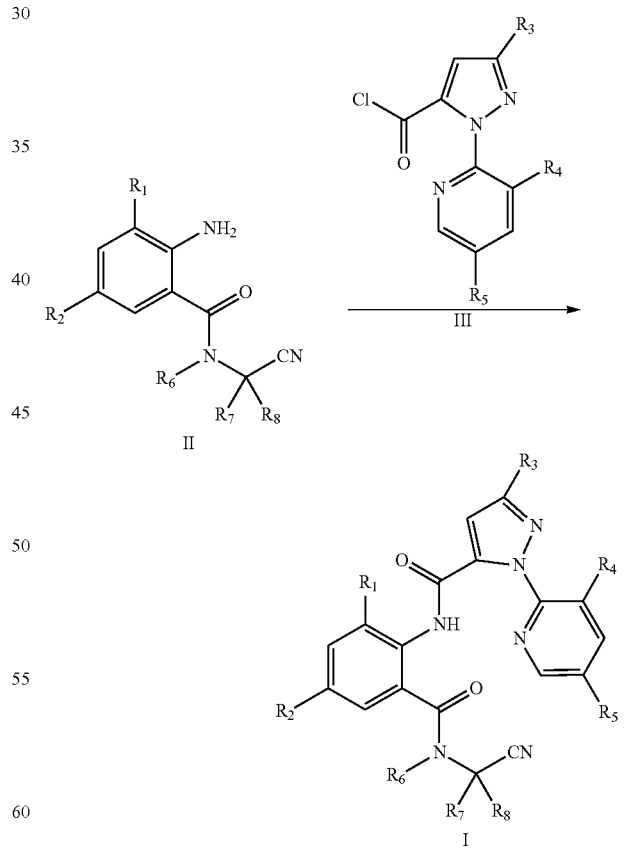

wherein
- $R_3$ is selected from halo, and $C_1$-$C_3$ haloalkyl;
- $R_4$ is selected from halo; and
- $R_5$ is selected from H or halo, wherein the obtained compound of General Formula I has an insecticidal activity of at least 90% when in a composition at 0.5 ppm concentration.

6. A process of preparing insecticides for controlling pests, comprising a step of dispersing an N-alkyl-N-cyanoalkylbenzamide compound of General Formula I in an acceptable carrier to prepare an insecticidal composition, wherein General Formula I has a structure of:

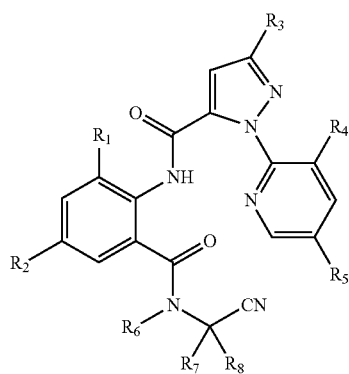

I wherein
$R_1$ is selected from halo or $C_1$-$C_3$ alkyl;
$R_2$ is selected from halo or CN;
$R_3$ is selected from halo, $C_1$-$C_3$ haloalkyl;
$R_4$ is selected from halo;
$R_5$ is selected from H or halo;
$R_6$ is selected from $C_1$-$C_3$ alkyl, $C_1$-$C_3$ haloalkyl or $C_1$-$C_5$ alkoxyalkyl;
$R_7$ is selected from $C_1$-$C_5$ alkyl; and
$R_8$ is selected from hydrogen or $C_1$-$C_5$ alkyl.

7. An insecticidal composition, comprising a compound of General Formula I according to claim 1, and an agriculturally, forestrically, and hygienically acceptable carrier, wherein the content in percentage by weight of the active ingredient in the composition is 0.1-99.5%.

8. A method for controlling pests, comprising applying an insecticidal composition according to claim 7 to the pests or their growth media in an effective amount of 10 g/hm$^2$-1000 g/hm$^2$, wherein $R_6$ is selected from $C_1$-$C_3$ alkyl.

9. The process of preparing insecticides for controlling pests according to claim 6, comprising a step of dispersing the N-alkyl-N-cyanoalkylbenzamide compound of General Formula I in an acceptable carrier to prepare an insecticidal composition, wherein,
$R_1$ is selected from chloro, bromo or methyl;
$R_2$ is selected from chloro, bromo, fluoro or CN;
$R_3$ is selected from chloro, bromo or trifluoromethyl;
$R_4$ is selected from chloro;
$R_5$ is selected from H or chloro;
$R_6$ is selected from $C_1$-$C_3$ alkyl, $CH_2OCH_3$, $CH_2OCH_2CH_3$, $CH_2CH_2OCH_3$, $CF_3$, $CH_2CH_2F$, $CH_2CHF_2$, $CH_2CF_3$, $CF_2CF_3$ or $CF(CF_3)_2$;
$R_7$ is selected from methyl; and
$R_8$ is selected from hydrogen or methyl.

10. The process of preparing insecticides for controlling pests according to claim 6, comprising a step of dispersing the N-alkyl-N-cyanoalkylbenzamide compound of General Formula I, wherein,
$R_1$ is selected from chloro, bromo or methyl;
$R_2$ is selected from chloro, bromo, fluoro or CN;
$R_3$ is selected from chloro or bromo;
$R_4$ is selected from chloro;
$R_5$ is selected from H;
$R_6$ is selected from methyl;
$R_7$ is selected from methyl; and
$R_8$ is selected from methyl.

* * * * *